United States Patent
Bjornstrup et al.

(10) Patent No.: US 8,518,452 B2
(45) Date of Patent: Aug. 27, 2013

(54) METHOD FOR STABILIZING BLOOD PLASMA COMPONENTS IN A LYOPHILIZATE USING CARBON DIOXIDE AND PHOSPHORIC ACID

(75) Inventors: Kim Bjornstrup, Feusisberg (CH); Martin Kern, Wolfsberg (AT); Andrea Heger, Vienna (AT); Gerhard Gruber, Vienna (AT); Hans Sachse, Vienna (AT); Raimund Schuetz, Vienna (AT); Juergen Roemisch, Gramatneusiedl (AT); Tor-Einar Svae, Moedling (AT)

(73) Assignee: Octapharma AG, Lachen (CH)

( * ) Notice: Subject to any disclaimer, the term of this patent is extended or adjusted under 35 U.S.C. 154(b) by 567 days.

(21) Appl. No.: 12/449,558

(22) PCT Filed: Feb. 15, 2008

(86) PCT No.: PCT/EP2008/051888
§ 371 (c)(1),
(2), (4) Date: Dec. 23, 2009

(87) PCT Pub. No.: WO2008/099016
PCT Pub. Date: Aug. 21, 2008

(65) Prior Publication Data
US 2010/0159023 A1    Jun. 24, 2010

(30) Foreign Application Priority Data
Feb. 15, 2007 (EP) ................................. 07102446

(51) Int. Cl.
*A61K 35/16* (2006.01)
(52) U.S. Cl.
USPC ........................................ 424/530; 424/531
(58) Field of Classification Search
None
See application file for complete search history.

(56) References Cited

U.S. PATENT DOCUMENTS

| | | |
|---|---|---|
| 5,309,649 A | 5/1994 | Bergmann et al. |
| 5,690,963 A | 11/1997 | Spargo et al. |
| 6,517,526 B1 | 2/2003 | Tamari |
| 6,773,425 B1 | 8/2004 | Tamari |
| 2004/0081588 A1 | 4/2004 | Hammerstedt et al. |
| 2005/0124589 A1 | 6/2005 | Roessler |

FOREIGN PATENT DOCUMENTS

| | | |
|---|---|---|
| EP | 0 124 018 | 11/1987 |
| EP | 0124018 | 11/1987 |
| EP | 0 284 249 | 9/1988 |
| EP | 0 343 596 | 11/1989 |
| EP | 1 308 170 A3 | 5/2003 |
| EP | 1 407 780 A1 | 4/2004 |
| EP | 1 417 972 A1 | 5/2004 |
| EP | 1870649 A1 * | 12/2007 |
| WO | WO 95/05845 | 3/1995 |
| WO | WO 95/27180 | 10/1995 |
| WO | WO 96/31748 | 10/1996 |
| WO | WO 01/24817 A3 | 4/2001 |

OTHER PUBLICATIONS

Bakaltcheva, I., "Freeze-dried whole plasma: Evaluating sucrose, trehalose, sorbitol, mannitol and glycine as stabilizer", Thrombosis Research, (2006), doi:10.1016/j.thromres2006.07.005, pp. 1-12.

* cited by examiner

*Primary Examiner* — Sandra Saucier
(74) *Attorney, Agent, or Firm* — Jacobson Holman, PLLC

(57) ABSTRACT

Process for the stabilization of blood plasma components in a lyophilizate, wherein
in a freeze-drying process, said blood plasma components were in a solution containing at least two different pH-lowering substances causing a predetermined pH value range to be adjusted in the solution formed upon reconstitution.

15 Claims, 1 Drawing Sheet

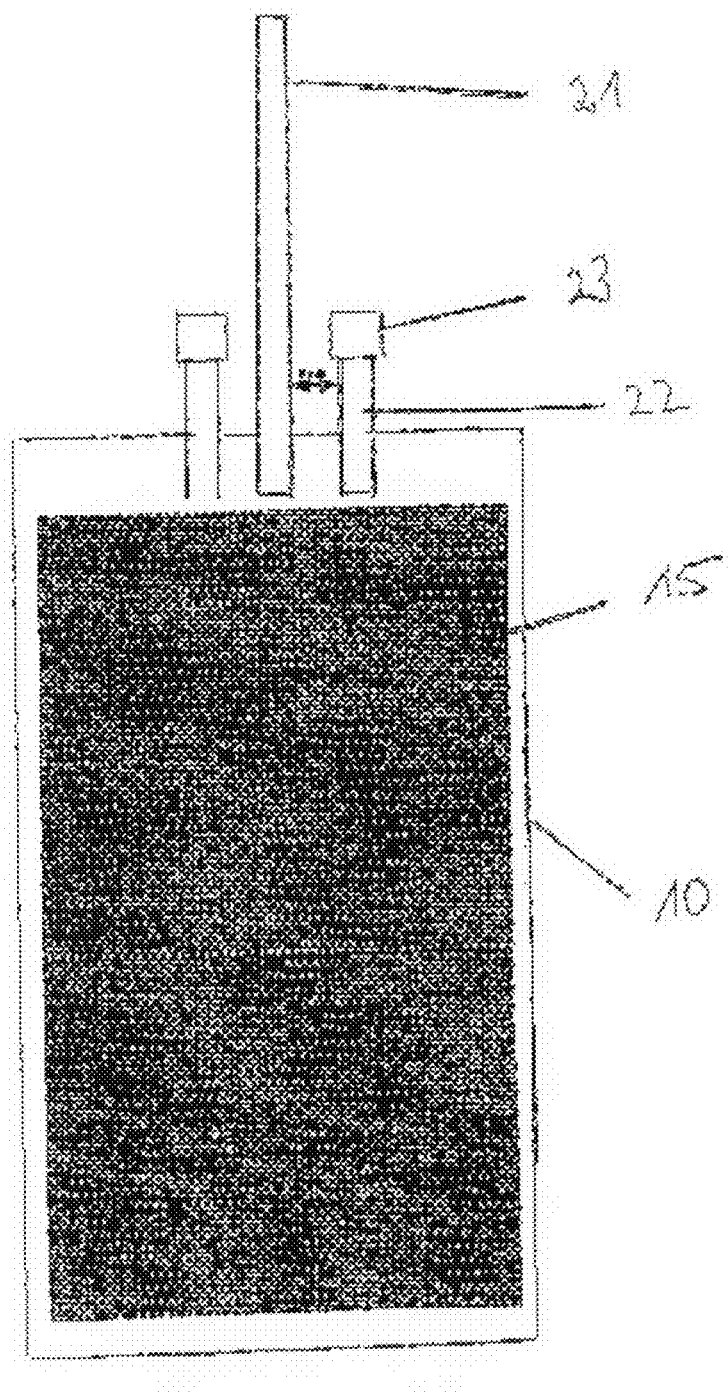

METHOD FOR STABILIZING BLOOD PLASMA COMPONENTS IN A LYOPHILIZATE USING CARBON DIOXIDE AND PHOSPHORIC ACID

This is a 371 of PCT/EP08/051888, filed Feb. 15, 2008, which claims the benefit of European 07102446.7, filed Feb. 15, 2007, the disclosure of which is incorporated herein by reference.

The present invention relates to a process for the stabilization of blood plasma components in a lyophilizate, and to the use of a container in the process according to the invention.

The storage of biopolymers, such as proteins, polysaccharides or nucleic acids and their mixtures, is effected in a soluble, frozen (aqueous) or lyophilized state depending on the demands made on the product. In the case of medicaments, all storage or dosage forms are used in accordance with stability or the kind of application. This also holds, for example, for solutions containing individual (purified) proteins or mixtures of proteins (biopharmaceuticals) or combinations thereof with other substances, such as lipids. Optionally, stabilizers especially optimized for the respective requirements are added in order to keep the product in a native and active state as long as possible.

For example, proteins isolated from blood plasma, such as coagulation factors (factors II, V, VII, VIII, von Willebrand factor (vWF), vWF/FVIII complex, FIX, X, XI, XII, XIII, fibrinogen, combinations thereof and activated forms thereof), FVII-activating protease (FSAP), protease inhibitors, for example, $\alpha$-1 antitrypsin, antithrombin III, heparin cofactor II, C1-esterase inhibitor, antiplasmin, protein C and its cofactors protein S, protein Z and other inhibitors, immunoglobulins, such as IgG, IgA, IgE, IgM and corresponding subclasses, proteins of fibrinolysis and of the complement system, such as plasminogen, plasminogen activators, complement factors, transport proteins, such as albumin, transferrin, growth factors and proteins supporting wound healing, such as hepatocyte growth factor, HGF, platelet-derived growth factor, PDGF, fibroblast growth factor, FGF, fibronectin, vitronectin etc. and combinations thereof, and plasma itself and its subfractions, such as cryoprecipitate and other subfractions familiar to the skilled person, such as intermediates from plasma fractionation according to Cohn, Kistler-Nitschmann and their modifications, stored in different states.

Immunoglobulins are used in liquid or lyophilized form depending on the product, the liquid variant being preferred in view of application and convenience because it makes prior reconstitution unnecessary.

In the case of plasma itself, which is used, for example, for transfusion purposes, liquid-stored, liquid-frozen as well as lyophilized variants are known and utilized depending on demands.

With intermediates from preparation processes for recombinant and transgenic products and for the final products, a corresponding procedure can be performed. Advantages of a lyophilized product are the possible storage for a comparably longer period of time at temperatures of above 0° C. up to room temperature and beyond, usually combined with a reduced weight (due to the reduced water content). Although a lyophilized product requires reconstitution in suitable solutions, the advantages are predominant in certain situations. Especially in emergency medicine, preferably in operations under very difficult treatment conditions, for example, outside of a professional hospital environment, a glass bottle is inferior to a more flexible and more lightweight material due to its weight and the possible risk of breaking. In addition, the cooling or thawing of the frozen product to be carried (such as plasma) is time-consuming.

The lyophilization of plasma or other protein solutions in glass bottles or ampoules is known to the skilled person. After the freeze-drying process has been completed, the vessels are closed with a suitable stopper in order to minimize the reentry of water vapor. This is usually unproblematic since the vessel openings are very small/narrow as compared to the total vessel and the surface area of the lyophilizate and thus the reabsorption of water (vapor) proceeds relatively slowly for normal ambient humidity. The dissolution of the product in case of need is achieved by adding water or other suitable solutions.

Properties of freeze drying and storage in glass containers that are disadvantageous in certain situations have been mentioned above in part. In addition, depending on the vessel opening, a relatively small exit surface area is available for freeze drying, which thus results in a correspondingly long lyophilization time. Therefore, what is also desirable is a process that enables the lyophilization to be accelerated without a faster uptake of moisture occurring to any significant extent during the later closing process.

The lyophilization process removes water vapor from the frozen material under embodiments known to the skilled person. In solutions that contain carbon dioxide, for example, the carbon dioxide may also be removed (at least partially), which may lead to a shift of the pH value towards basicity of the resulting product after reconstitution with water or other solutions. This is observed, for example, with protein-containing solutions, such as blood plasma. A pH value of 7.0-7.6 before freeze-drying may achieve a pH value of above 8.0 after reconstitution, as further explained in the Example given below. This pH shift may have consequences for the product and the patient. In particular, the integrity of certain active components or their stability over an extended period of time may be adversely affected. In addition, the more basic pH of the reconstituted product requires an enhanced attention regarding the transfusion-receiving patient during the application if greater volumes are applied.

US-A-2005/0124589 relates to the reconstitution of ifosfamide lyophilizate with a buffer solution.

EP-A-1 417 972 relates to stabilized teriparatide solutions containing mannitol acetate or tartrate as well as m-kresol or benzyl alcohol as a preservative.

WO-A-01/24817 discloses the reconstitution of a lyophilized composition of fibrolase or a thrombolytic agent, the pH value being maintained at pH 8.0. Fibrolase is an enzyme obtained from snake venom.

EP-A-0 284 249 relates to the lyophilization of lymphokines, and EP-B-0 124 018 relates to the preparation of a lyophilized fibronectin formulation adjusted to a pH value of from 6.5 to 7.5 prior to lyophilization.

WO-A-95/05845 relates to the preparation of a lyophilized nerve growth factor formulation, the composition having a pH value of 5.2 after reconstitution with a solution of sodium chloride and citric acid.

An object of the invention was to provide an improved process by which the described drawbacks in the handling of lyophilizates, especially in medical application, are avoided or at least reduced.

This object is achieved by a process for the stabilization of blood plasma components in a lyophilizate, wherein
  in a freeze-drying process, said blood plasma components
    were in a solution containing at least two different pH-lowering substances causing a predetermined pH value range to be adjusted in the solution formed upon reconstitution.

The process according to the invention enables the skilled person to counterbalance a pH shift to be expected or taking place upon reconstitution by suitable measures.

The protocol according to the invention, i.e., to use at least two different substances, advantageously allows to provide a lyophilizate that already has the desirable pH value after uptake in aqueous solutions for reconstitution. This is advantageous over adjusting the pH with a single substance, since in the latter case, it is not ensured that the concentration of buffer substance remains below the permitted limits.

In a preferred embodiment of the process according to the invention, a total of three measures are employed for regulation, namely on the one hand treatment of the product to be lyophilized with $CO_2$ gas, for example, to a pH of the solution of from 6.5 to 7, then adding a mineral acid, especially phosphoric acid to achieve a further lowering, for example, by 0.2 pH units, and finally addition of another acid which is different from the first acid, for example, citric acid, in order to achieve another pH lowering, for example, by another 0.2 to 0.3 pH units. A thus prepared sample may then by lyophilized to achieve the desired pH in the reconstituted solution which is not deleterious to the active protein present in the solution. Thus, the invention also provides the skilled person with a technical teaching as to how simple routine experiments may be used to establish with what precise quantities a pH that is optimum for the system in question can be set.

The term "solution" according to the invention is understood to mean a system in which the components are dissolved in an essentially aqueous phase, i.e., rather than in a phase containing an undissolved solids fraction as described in U.S. Pat. No. 5,690,963.

In the process according to the invention, it may be intended that said at least two substances prevent an adjustment of the pH into ranges which negatively affect the structure of the blood plasma components in the lyophilizate by an at least partial loss of activity and/or nativity, denaturing, fragmentation, aggregation, chemical modification, such as oxidation.

By lowering the pH in the solution to be lyophilized into a range that does not affect the blood plasma components, for example, main active components of the product, it can be achieved that the pH of the product is in said predetermined pH range after lyophilization and reconstitution. For plasma, said predetermined range may be typically a pH range of from pH 6.95 to 7.9, especially from pH 7.0 to 7.6, but may require rather different pH values for other biopolymer solutions. The pH values that are to be adjusted in each case may be established, unless known to the skilled person anyway, by simple experiments by determining essential parameters of the components, such as nativity, effectiveness, aggregation behavior etc., for example, under different pH conditions.

In one embodiment of the process according to the invention, said adjusting of the pH value is the lowering of the pH value in terms of a resulting more acidic solution before lyophilization by adding suitable substances, buffer solutions or (dilute) acid solutions to achieve a desired pH value after reconstitution of the product.

The adjusting of the pH range of the solution before the lyophilization can be done in such a way that a pH value that is to be present after reconstitution in the solution formed thereby (predetermined pH value or pH range) when the lyophilizate is reconstituted with a reconstitution solution. Namely, without adjustment, the pH value of the reconstituted solution can deviate significantly from the pH value of the solution before freeze drying if this is tolerable. Thus, for example, a solution with blood plasma components having a pH value of 7.4 can be adjusted to 6.0 to reach a pH range of from 6.6 to 7.0 after reconstitution, for example, with water.

Another possibility to achieve the sought pH value after reconstitution of the product is to adjust the pH value during or after the dissolving of the lyophilizate. This can be done by adjusting the product solution with suitable buffer solutions or by subsequent incorporation of correspondingly acidified solutions. The individual titration of each individual vessel or of removed solutions takes time and is little practical in terms of a rapid and safe application, such as a transfusion. However, dissolving the product with a suitable solution having per se acidic properties and leading to the sought pH value of the product is also a practical measure.

In the process according to the invention, for example, buffer substances, such as salts of mineral or organic acids and bases, especially phosphates or carbonates, are employed as substances, wherein the pH value can also be adjusted by introducing $CO_2$. Further, di- or monohydrogenphosphates, hydrogencarbonates, hydrogensulfates, salts of organic acids or bases, tris(hydroxymethylamino)-methane and/or amino acids may be employed as substances for adjusting the predetermined pH value. In particular, the reconstitution of the lyophilizate may be done in an aqueous solution containing physiologically acceptable acidic-hydrolyzing salts or physiologically acceptable acids.

The reconstitution may advantageously be effected with essentially neutral water for injection if the freeze drying of the blood plasma components is done in a solution containing substances that cause a predetermined pH range to be adjusted in the solution formed during the reconstitution.

The procedure according to the invention is further explained in an exemplary manner. The acidification of the product before lyophilization can be effected with suitable solutions and substances that enable a corresponding adjustment to the pH range after dissolution of the product obtained. Citric acid in a suitable concentration can be used, for example, to bring the pH value of the plasma to the pH range pf pH 6.0-6.95, preferably pH 6.5-6.95, to achieve a pH value of from 7.0 to 7.9 upon reconstitution of the lyophilized plasma. Particularly preferred is the addition of citric acid in a concentration range of 0.1-20.0 mM (final concentration of the added solution in the product), preferably 1-5 mM, for plasma. Citric acid solutions for the reconstitution of lyophilized plasma are also within these concentration ranges. For other protein solutions in terms of pH adjustment before lyophilization and during reconstitution, the addition of citric acid in a concentration range of 0.1-50 mM (final concentration in the product of the added acid) is useful. It may be noted that the resulting citric acid content or the resulting citrate content in the product may be higher in total if citric acid/citrate was present already before the addition. This also applies, *mutatis mutandis*, to other substances that may be added for such adjustment, such as phosphate buffers etc.

Accordingly, other agents and the addition of other buffer and acid solutions are possible. It is to be mentioned that the pH value of the solution may also be effected by introducing $CO_2$ gas into the solution (supplying gas to the surface with stirring the solution or by introducing a flexible tube into the solution or similar techniques familiar to the skilled person) before lyophilization.

In contrast, lyophilized vessels may also be exposed to an acidic atmosphere prior to packaging, as described above. For example, diffusion into the vessels may be effected by introducing $CO_2$ in the form of gas, so that the resulting lyophilizate and later the corresponding product solution reaches the desired pH value.

The described measures for adjusting the desired pH value before the lyophilization, during the storage of the product and during reconstitution can be achieved by the measures described. These may be employed singly or in combination. Thus, it is also possible to store the lyophilizate under acidic pH conditions, as is advantageous and known, for example, for immunoglobulins, followed by dissolving them in water and maintaining the acidic medium to prevent rapid aggregation of the component or components.

Adjustment of the pH value for product solutions before administration to the patient may also be necessary in order to achieve the required treatment effect.

In the solution to be lyophilized and/or a reconstitution solution, stabilizers of the blood plasma components, especially of therapeutically important blood plasma components, may be present. As stabilizers, polysaccharides, oligosaccharides, for example, sugars, polyols, for example, mannitol or sorbitol, amino acids or combinations thereof may be mentioned, in particular.

In another embodiment of the process according to the invention, the lyophilizate is obtained by having the blood plasma components in an essentially aqueous solution and filling it in a container which at least partially consists of a sterile material that is impermeable to water, but permeable to water vapor, and preventing the uptake of water vapor beyond a predetermined residual moisture content of the lyophilizate after the freeze drying process has been completed.

Numerous containers for performing lyophilizations are known. Thus, US-A-2004/0081588 relates to a container allowing for shrinkage during the lyophilization process and containing microporous walls made of a membrane permeable to water vapor, but impermeable to water.

U.S. Pat. No. 6,773,425 relates to a container for collecting, freeze-drying, storing, reconstituting, and administering biological solutions and, in particular, blood products.

EP-A-0 343 596 relates to a process and container for freeze drying under sterile conditions. The container disclosed in the specification has sides with an at least partially hydrophobic, porous, germ-tight membrane permeable to water vapor.

WO-A-95/27180 relates to containers for minimizing the contamination of freeze-dried products. The container in question also has a site that allows water vapor to escape.

WO-A-96/31748 relates to a bag for receiving solutions to be freeze-dried, also having a sterile barrier permeable to water vapor that is provided on a backing material.

In this connection, it may be mentioned that the so-called residual moisture content of the lyophilizate is very important to the storage stability of the product in many cases. Lyophilizates with sensitive blood plasma components, for example, therapeutic proteins, should be stored below 5% residual moisture depending on the storage conditions (temperatures), preferably below 3%, in order to enable enduring activity, nativity and safety.

The rapid re-entry of water vapor into the plastic container can be prevented or hampered by several measures in the process according to the invention. Reduction of the relative atmospheric humidity in the removal region and/or flooding the lyophilizer with nitrogen or other suitable measures are practical. In particular, the rapid covering or sealing of the membrane surface by suitable measures, such as applying water-vapor impermeable and sterile sheets or the rapid closing of the containers into suitable sheet bags can hamper or even prevent the uptake of moisture. This can be done under nitrogen or with evacuation of the bags. In addition or alternatively, a material for binding water (vapor) known to the skilled person may be added to the bag, depending on what range of residual moisture is to be adjusted.

It may be recommendable to place on a support material said container made of a sterile material that is impermeable to water, but permeable to water-vapor.

On some occasions, blood plasma components have already been mentioned that may be present in the lyophilizate which can be reconstituted according to the invention. However, the process according to the invention is not limited to such blood plasma proteins. Of therapeutical importance as blood plasma components are, in particular, proteins from blood, plasma or serum as well as recombinantly or transgenically prepared blood plasma proteins.

Illustratively, there may be mentioned, in particular, proteins isolated from blood plasma, such as coagulation factors (factors II, V, VII, VIII, von Willebrand factor (vWF), vWF/FVIII complex, FIX, X, XI, XII, XIII, fibrinogen, combinations thereof and activated forms thereof), FVII-activating protease (FSAP), protease inhibitors, for example, $\alpha$-1 antitrypsin, antithrombin III, heparin cofactor II, C1-esterase inhibitor, antiplasmin, protein C and its cofactors protein S, protein Z and other inhibitors, immunoglobulins, such as IgG, IgA, IgE, IgM and corresponding subclasses, proteins of fibrinolysis and of the complement system, such as plasminogen, plasminogen activators, complement factors, transport proteins, such as albumin, transferrin, growth factors and proteins supporting wound healing, such as hepatocyte growth factor, HGF, platelet-derived growth factor, PDGF, fibroblast growth factor, FGF, fibronectin, vitronectin etc. and combinations thereof, and plasma itself (in the form of, e.g., citrated plasma, oxalated or heparinized plasma) and its subfractions, such as cryoprecipitate and other subfractions familiar to the skilled person, such as intermediates from plasma fractionation according to Cohn, Kistler-Nitschmann and their modifications.

Similarly, blood plasma components contained in biological sources, such as body fluids, or fractions of transgenic or recombinantly prepared proteins may also be contemplated.

In a particular embodiment, the process according to the invention is performed in containers in which the sterile material permeable to water vapor consists of fluorinated plastic materials, polyester or polyethylene.

In order to shorten the relatively long duration of lyophilization, which is found disadvantageous, as large as possible a surface, suitable for water vapor exit, as compared to the (frozen) product surface is provided in this embodiment of the process according to the invention. To reduce the total container weight and for easier handling, plastic materials in the form of suitable containers, such as bags, may also be used as support material for the containers in which the lyophilization takes place. These may consist of materials such as polypropylene, polyethylene, ethyl vinyl acetate, polyvinyl chloride, polyurethane or other suitable materials or combinations thereof, and layers such as those of the Kraton® polymer type, which may consist of multilayer systems known to the skilled person, and combinations thereof with other materials. The Kraton® polymers are block polymers of styrene/butadiene/styrene, styrene/isoprene/styrene, styrene/ethylene-butylene/styrene, styrene/ethylene-propylene/styrene, each of which may also bear functional groups, such as maleic anhydride.

These materials are not usually permeable to water vapor, so that a membrane permeable to water vapor may be used to ensure that a suitably high gas exchange can occur during the freeze drying. Such membranes may consist of polytetrafluoroethylene (fluoropolymers), polypropylene, polyethylene or other suitable membranes and their combinations. Every membrane material is not simply compatible with the bag material in terms of a tightly preparable bond, e.g., weld. Corresponding combinations are combined by techniques familiar to the skilled person, for example, by thermal welding and/or mechanical anchoring or other suitable methods. Preferred combinations are container materials of polypropylene and/or Kraton polymers with membranes based on fluoropolymer material, preferably polytetrafluoroethylene or polypropylenes, and preferably containers of polyethylene with polyethylene-based membranes, such as the so-called high density polyethylenes. Multilayer systems also lend themselves as a basis for containers in order to ensure stability, sterility and water and gas tightness and can be bonded to suitable membrane materials.

The membranes may form the whole bag, but usually it will be preferable to have only part of the bag in the form of such a membrane. One reason for this is that the lyophilization usually takes place in such a way that the plastic container in the lyophilizer rests on a solid surface (cooled, to be cooled), and thus part of the membrane surface is not available for the maximum water vapor exit. Further, the re-entry of water vapor into the lyophilizer after the lyophilizer is opened will usually be clearly accelerated as compared to a plastic container with an optimized membrane fraction.

One particular embodiment of such a container is, for example, a bag of polypropylene whose surface consists on one side thereof of a large proportion (>50% of this one-side surface facing the lyophilizer space) of the membrane which is freely accessible during lyophilization, i.e., facing away from the cooling surface onto which the device is placed. The membrane fraction of this accessible surface should be as large as possible in order that the freeze drying process can occur effectively. For example, if the membrane surface is too small as compared to the bag surface (e.g., if the membrane edge is too remote from the bag edge and the solution provided below), the water vapor molecules must move horizontally at first through the solution/lyophilizate during the evaporation in order that they can exit through the membrane. In addition to a prolonged lyophilization time, this may lead to undesirable inhomogeneities of the lyophilizate (region of incomplete drying, inclusions).

What is also useful in the process according to the invention is to place the container permeable to water vapor into a container impermeable to water vapor, which may consist of plastic materials or aluminum foil.

The process according to the invention can be performed in the lyophilization processes familiar to the skilled person. In particular, this may also be done in a process in which a freeze-drying process is applied that includes first and second steps, wherein a lower input of desorption energy into the freeze-drying process occurs in the second step of the freeze-drying process as compared to the first step. This process is a subject matter of US 20080172902, where it is described in more detail. US 20080172902 is included herein by reference.

The process according to the invention can be performed, in particular, using a container as schematically represented in the Figure. The container for lyophilization has walls 10 and connection elements 21, 22. The walls 10 at least partially consist of a sterile material 15 that is impermeable to water, but permeable to water vapor. The connection element 22 can be designed as a short projecting connector and closed by a septum 23. The filling of the bag may be effected, for example, through the filling hose 21. The wall 10 is interrupted here by the window 15 in the visible part thereof. The window 15 consists of a material permeable to water vapor, but impermeable to water. This material is described in detail above.

In the following, the invention will be further illustrated by means of the Examples.

EXAMPLE 1

The object of this experiment was to examine basically the kinetics of the reabsorption of water vapor by the lyophilized product and the influence of the ambient temperature and the atmospheric humidity. Thus, glass bottles (20 ml) having a narrow neck/entry were filled with 5 ml of plasma each (1 cm filling level) and lyophilized. The controls were sealed airtight, whereas other bottles were stored either at room temperature/60% atmospheric humidity or at 40° C./75% atmospheric humidity for up to 7 hours, the gas space of the bottles being shortly flushed with nitrogen gas and the bottles sealed airtight. The analysis of the residual moisture contents of the lyophilizates was performed by the Karl Fischer method, which is known to the skilled person.

|  | Residual moisture content [%] | Increase of residual moisture [%] |
|---|---|---|
| Room temp., 60% | | |
| 0 h | 0.86 (0.81-1.01) | — |
| 1 h | 3.30 (2.82-3.54) | +2.44% |
| 2 h | 5.81 (5.65-5.95) | +4.95% |
| 7 h | 10.91 (10.57-11.20) | +10.05% |
| 40° C., 75% atmospheric humidity | | |
| 0 h | 0.86 (0.81-1.01) | — |
| 1 h | 5.95 (5.93-6.01) | +5.09% |
| 2 h | 8.97 (8.57-9.21) | +8.11% |
| 7 h | 16.65 (15.93-17.07) | +15.79% |

Result:

The results show that the increase of residual moisture in the lyophilizate occurs relatively quickly and depends on the ambient temperature and atmospheric humidity. Accordingly, measures can be taken to limit an undesirably high residual moisture content. The control samples (0 hours, i.e., directly after removal from the lyophilizer) show that the residual moisture can be kept in a desired range in a suitable process (quick airtight sealing).

EXAMPLE 2

In this Example, the knowledge gained above was taken into account by sealing the lyophilizate-containing containers airtight in a plastic bag immediately after removal from the lyophilizer.

For this purpose, polypropylene containers in the form of a bag as outlined in the Figure were used, wherein the polytetrafluoroethylene membrane was applied two-dimensionally on one side thereof (after preparation of a corresponding window on one side of the bag) to result in a liquid-tight bond. Inlet and outlet elements for filling the bag and optionally quick venting in terms of displacement of the air present in the bag by the entering liquid are provided. In addition, the inlet and outlet elements also enable the incorporation of a reconstitution liquid after freeze drying and an outlet for the reconstituted solution to be removed in the practical application for infusion into the patient. These inlet/outlet connections may consist of plastic materials known to the skilled person, polypropylene in the Example described.

After sterilization of the containers, 200 ml each of blood plasma was filled into these bags under sterile conditions, the inlet connection was heat-sealed, the bags were frozen, and freeze drying was performed. After drying, the bags were removed from the lyophilizer and immediately heat-sealed airtight in plastic bags.

For the reconstitution of the lyophilizates, the lyophilizate-containing containers were removed from the protective bags (after cutting them open), followed by adding 184 ml of liquid as described below to obtain a final volume of 200 ml of reconstituted plasma. With slight rocking of the bags, complete reconstitution to form a clear solution was effected within 5 minutes.

Residual Moisture Content:

The analysis of the lyophilizates after storage of the bags showed residual moisture contents of from 1.0 to 1.5% for the containers that were sealed in the bags very quickly, and a residual moisture of from 2.0 to 2.5% if the containers were packaged with delay. These results were reproducible for containers that had been stored for days and several weeks, sealed in bags. In contrast, lyophilizates that had not been heat-sealed in appropriate bags for hours showed residual moisture contents of clearly above 3%, as could be assumed in principle from the result of Example 1.

EXAMPLE 3

The same procedure as set forth in Example 2 was employed including the use of the plastic materials, freeze-drying conditions and handling. The containers in the form of bags containing a membrane fraction were filled with 200 ml of plasma. In this Example, a coagulation-promoting solvent/detergent-treated human blood plasma and the universally applicable blood plasma according to WO-A-2005/058334 or EP-A-0 991 416 were used. Both coagulation-promoting products are produced after thawing and pooling up to 1,520 single plasma donations by means of a strictly supervised preparation process under GMP conditions. The solvent/detergent method implemented in the production process reaches a very high degree of safety in terms of minimizing the residual infection risk (for transfusion-relevant enveloped viruses), and individual donor screening and other safety measures and effective process steps also contribute significantly to the safety of the products. Universally applicable plasma is obtained by an optimum integration of individual donations of blood types A, B and AB in described mixing ratios (as described in EP-A-0 991 416 and EP-A-1 696 940), which enables application with the patient independently of blood types.

The subsequent preparation process for a human blood plasma was performed according to P. Hellstern et al., Vox Sang 1992; 63: 178-185.

Individual donor plasmas or individual and pool plasma products treated by other methods as well as polymers within the meaning of the invention may be used. Three different samples were examined in this Example, and a control sample was included:

A. To the S/D treated plasma pool (human blood plasma and universally applicable plasma method), citric acid was added dropwise with thorough mixing by stirring to a final concentration of the "added citric acid" of 3-4 mM, the pH value being lowered from pH 7.0-7.4 to pH 6.5-6.7. After sterile filtration, the resulting plasma was filled into the containers for subsequent freeze drying. The reconstitution of the lyophilizates was effected by adding 184 ml each of water for injection (WFI).

B. Human blood plasma/universally applicable plasma was prepared without adding pH-lowering solutions and filled into bags. The reconstitution of the lyophilizates was effected by adding 184 ml each of WFI containing citric acid at a concentration of 3-4 mM.

C. Human blood plasma/universally applicable plasma was prepared without adding pH-lowering solutions and filled into bags. The reconstitution of the lyophilizates was effected by adding 184 ml each of WFI, but without added citric acid.

D. Human blood plasma/universally applicable plasma was filled into commercially available bags and stored frozen. The non-lyophilized product was used as a control.

Representative containers of each sample were reconstituted as described above (or after thawing), and the individual pH values were measured. In addition, important coagulation factors (factors II, V, VII, VIII, IX, X, XI, XII, XIII, ADAMTS13), inhibitors (antithrombin III, proteins C and S, alpha-1 antitrypsin, antiplasmin and C1 inhibitor) were quantified by activity tests as known to the skilled person. In addition, so-called global coagulation parameters were determined, which may give an indication of any deteriorations of one or more factors: activated partial thromboplastin time (aPTT), prothrombin time (PT), thrombin time (TT) and reptilase time (RT). Any activations of factors are indicated by so-called markers, such as the thrombin-antithrombin complex (TAT), prothrombin fragments (F1+2), activated factor VII (FVIIa) and D dimers.

Result:

Individual pH Values

Sample A: pH 7.5 to 7.9
Sample B: pH 7.3 to 7.6
Sample C: pH 8.1 to 8.4
Control: pH 7.0-7.4

Samples A and B showed no loss of activities within the experimental error (+/−20% relative to the controls) for all test parameters as described above. A significant change of the concentrations of activation markers was not found.

In contrast, the reconstituted samples C showed lowered activities of factor VIII and protein S as compared to the control as well as an extended reptilase time.

In order to avoid a significant influence on the quality of the reconstituted product, the pH value may be adjusted before the lyophilization to arrive at the desired pH range (A) or by reconstitution with a corresponding solution (B).

EXAMPLE 4

In this Example, the influence of pH adjustments before lyophilization by adding individual pH-lowering components and their combinations was tested in order to examine their influence on the pH values in the corresponding lyophilizates or after reconstitution thereof (in water, WFI). As a starting sample for the experiments, pool plasma having an initial pH value of 7.4 was used. Three different test samples were prepared, and a control sample was included.

A. Plasma pool (control sample).

B. The pH value was adjusted to 6.9 in the plasma pool by introducing $CO_2$ gas. Subsequently, phosphoric acid was added to the plasma pool dropwise with thorough mixing by stirring to a final concentration of the added phosphoric acid of 2 mM, the pH value being (further) lowered to 6.7.

C. To the plasma pool in sample B, citric acid was additionally added dropwise with thorough mixing by stirring to a final concentration of the added citric acid of 1 mM, the pH value being (further) lowered to 6.5.

D. To the plasma pool in sample B, citric acid was additionally added dropwise with thorough mixing by stirring to a final concentration of the added citric acid of 2 mM, the pH value being (further) lowered to 6.4.

The plasmas from samples A-D were filled in the containers for subsequent freeze drying. The pH values respectively before the lyophilization and respectively after reconstitution of the lyophilizates of each sample with WFI were measured as summarized in the Table.

Result:

| pH value | Control (pH) | | Test samples (pH) | |
|---|---|---|---|---|
| | A | B | C | D |
| in the plasma pool | 7.4 | 7.4 | 7.4 | 7.4 |
| in the plasma after introduction of $CO_2$ | — | 6.9 | 6.9 | 6.9 |
| in the plasma after addition of 2 mM phosphoric acid | — | 6.7 | 6.7 | 6.7 |
| in the plasma after addition of 1 mM citric acid | — | — | 6.5 | — |
| in the plasma after addition of 2 mM citric acid | — | — | — | 6.4 |
| in the reconstituted plasma | 8.5 | 8.0 | 7.8 | 7.6 |

The results of the samples show that the desired pH ranges in the reconstituted plasma lyophilizates can be adjusted by the addition/treatment or a combination thereof of/with different pH-lowering components before the lyophilization.

The invention claimed is:

1. In a process of freeze-drying blood plasma components to form a lyophilizate, the improvement wherein, prior to freeze-drying, combining at least different pH-lowering substances carbon dioxide and phosphoric acid with the blood plasma components in aqueous solution, thereby effecting a predetermined pH value range in a reconstituted solution of the components.

2. The process according to claim 1, wherein
freeze-drying occurs in a first container including a sterile material that is impermeable to water but permeable to water vapor and
after freeze-drying uptake of water vapor beyond a predetermined residual moisture content of the lyophilizate is prevented.

3. The process according to claim 2, wherein the sterile material is provided on a support.

4. The process according to claim 3, wherein the support is made of material selected from the group consisting of polypropylene, polyethylene, ethyl vinyl acetate, polyurethane, and block polymers of styrene/butadiene/styrene, styrene/isoprene/styrene, styrene/ethylene/butylene/styrene, styrene/ethylene/propylene/styrene, and combinations thereof.

5. The process according to claim 2, wherein the sterile material is a fluorinated plastic material, polyester, or polyethylene.

6. The process according to claim 2, wherein the first container is disposed in a second container impermeable to water vapor and made of a plastic material or aluminum foil.

7. The process according to claim 2, wherein the first container has walls and connection elements, wherein the walls comprise a sterile material that is impermeable to water but permeable to water vapor.

8. The process according to claim 1, wherein the at least two different pH-lowering substances prevent the pH value from being adjusted into ranges that negatively affect the structure of the blood plasma components in the lyophilizate by an at least partial loss of activity and/or nativity, denaturing, fragmentation, aggregation, or chemical modification.

9. The process according to claim 1, wherein the blood plasma components are selected from the group consisting of proteins, polysaccharides, nucleic acids, lipids, and mixtures thereof.

10. The process according to claim 1, wherein the blood plasma components are proteins from blood, plasma, or serum.

11. The process according to claim 1, wherein the aqueous solution further comprises a stabilizer selected from the group consisting of sugar, polysaccharides, oligosaccharides, polyols, amino acids, and combinations thereof.

12. The process according to claim 1, wherein the blood plasma components are fractions of transgenic or recombinantly prepared proteins.

13. The process according to claim 1, wherein the freeze-drying comprises (i) a first step and (ii) a second step having a lower input of desorption energy than the first step.

14. A process comprising reconstituting a lyophilizate in an aqueous solution containing physiologically acceptable acid-hydrolyzing salts or physiologically acceptable acids, wherein the lyophilizate is obtained by the process of claim 1.

15. A process comprising reconstituting a lyophilizate with neutral water for injection, wherein the lyophilizate is obtained by the process of claim 1.

* * * * *